US008140303B2

(12) United States Patent
Terashita (10) Patent No.: US 8,140,303 B2
(45) Date of Patent: Mar. 20, 2012

(54) BIOEQUIVALENCE EVALUATION METHOD OF EVALUATING BIOEQUIVALENCE OF A GENERIC DRUG TO THE CORRESPONDING ORIGINAL DRUG

(76) Inventor: Masato Terashita, Tsu (JP)

( * ) Notice: Subject to any disclaimer, the term of this patent is extended or adjusted under 35 U.S.C. 154(b) by 0 days.

(21) Appl. No.: 12/599,603

(22) PCT Filed: Dec. 24, 2008

(86) PCT No.: PCT/JP2008/073374
§ 371 (c)(1),
(2), (4) Date: Dec. 21, 2009

(87) PCT Pub. No.: WO2009/090837
PCT Pub. Date: Jul. 23, 2009

(65) Prior Publication Data
US 2010/0274494 A1    Oct. 28, 2010

(30) Foreign Application Priority Data

Jan. 15, 2008   (JP) .................................. 2008-006222

(51) Int. Cl.
*G06F 17/10* (2006.01)
(52) U.S. Cl. ............. 703/2; 702/19; 702/30; 211/41.12; 514/1; 424/9.1
(58) Field of Classification Search .......................... None
See application file for complete search history.

(56) References Cited

U.S. PATENT DOCUMENTS
2004/0253180 A1   12/2004   Foster et al.

FOREIGN PATENT DOCUMENTS
WO    WO 03/093503 A2    11/2003

OTHER PUBLICATIONS

Kharidia et al. "Use of Truncated Areas to Measure Extent of Drug Absorption in Bioequivalence Studies: Effects of Drug Absorption Rate and Elimination Rate Variability on this Metric", 1999, Pharmaceutical Research, vol. 16, pp. 130-134.*
Creticos et al. "A methacholine challenge dose-response study for development of a pharmacodynamic bioequivalence methodology for albuterol metered-dose inhalers", 2002, Journal of Allergy and Clinical Immunology, pp. 713-720.*
Nobuo Aoyagi, "Regulatory Action for Bioequivalence of Generic Drugs," Chromatography, vol. 28 Supplement 1, pp. 19-22, 2007 with English Abstract.
Nakamura et al., "Variation in Biological Equivalency Test among Generic Drugs," Jpn. J. Pharm. Health Care Sci. vol. 31, No. 2, pp. 158-163, 2005 with English Abstract.

Summary of the 41st Japan Pharmaceutical Association Congress of Pharmacy & Pharmaceutical Science in Miyazaki held on Oct. 12 and 13, 2008 with English Abstract.
Hirayama et al., "Problems of Generic Drugs: Bioequivalence Test and Difference in Subjects in Generic Drug," Drug Preparation and Information (Rx Info), vol. 12, No. 10, pp. 1235-1242, 2006 with English Abstract.
Nakamura et al., For Selection of Excellent Generic Drug (4), Evaluation of Bioequivalence, lyaku (Medicine and Drug) Journal, vol. 43, No. 6, pp. 1569-1575, 2007 with English Abstract.
Nobuo Aoyagi, "Bioequivalence Tests of WHO and Japan," Pharmaceutical Regulatory Science, vol. 28, No. 5. pp. 355-369, 1997 with English Abstract.
International Search Report issued on Mar. 17, 2009 in PCT/JP2008/073374.
D.W. Jeong et al., "Analysis of carvedilol in human plasma using hydrophilic interaction liquid chromatography with tandem mass spectrometry." Journal of Pharmaceutical and Biomedical Analysis, vol. 44, pp. 547-552, 2007.
Extended European Search Report issued on Sep. 2, 2011 in European Patent Application No. 08 87 0659.
G.A. Smith et al., "An Automated Method for the Determination of Montelukast in Human Plasma Using Dual-Column HPLC Analysis and Peak Height Summation of the Parent Compound and its Photodegradation Product." Pharmaceutical Research, vol. 21, No. 9, pp. 1539-1544, Sep. 2004.
H. Farrar et al., "Vaildation of a liquid chromatographic method for the determination of ibuprofen in human plasma," Journal of Chromatography B, vol. 780, pp. 341-348, 2002.
H.N. Mistri et al., "Liquid chromatography tandem mass spectrometry method for simultaneous determination of antidiabetic drugs metformin and glyburide in human plasma," Journal of Pharmaceutical and Biomedical Analysis, vol. 45, pp. 97-106, 2007.
J. Park et al., "Quantification of gliclazide by semi-micro high-performance liquid chromatography: applicatin to a bioequivalence study of two formulations in healthy subjects," Journal of Pharmaceutical and Biomedical Analysis, vol. 35, pp. 943-949, 2004.

* cited by examiner

*Primary Examiner* — Carolyn L. Smith
(74) *Attorney, Agent, or Firm* — Birch, Stewart, Kolasch & Birch, LLP (57) ABSTRACT

[Problem] There is provided a bioequivalence evaluation method not only of evaluating bioequivalence between an original drug and a corresponding generic drug but also of enabling to compare bioequivalence between generic drugs. [Means of Solving the Problem] The bioequivalence between generic drugs is evaluated according to the Expression (1) wherein $CCV_{Cmax\ g}$ stands for the calibration coefficient of variation of Cmax (the maximum blood concentration), $CCV_{Tmax\ g}$ stands for the calibration coefficient of variation of Tmax (the time to maximum blood concentration), $CCV_{T1/2\ g}$ stands for the calibration coefficient of variation of the half-life ($T_{1/2}$), and $CCV_{AUC\ g}$ stands for the calibration coefficient of variation of AUC (the blood concentration-area under the curve).

9 Claims, 11 Drawing Sheets

| ID | name of commodities | pngn | content | maker | number of subjects | auc | aucsd |
|---|---|---|---|---|---|---|---|
| 27 | Calvadine | g | 20mg | sawai | 24 | 26.29 | 14.33 |
| 28 | Calvadine | standard | 20mg | sawai | 24 | 25.84 | 16.21 |
| 31 | JIMROST | g | 20mg | TOWA PHARMACEUTICAL CO., LTD. | 24 | 32.894 | 15.674 |
| 32 | JIMROST | standard | 20mg | TOWA PHARMACEUTICAL CO., LTD. | 24 | 33.778 | 15.553 |
| 35 | Kaoltone | g | 20mg | Nissin Pharmaceutical Co.,LTD | 24 | 36.82 | 11.1 |
| 36 | Kaoltone | standard | 20mg | Nissin Pharmaceutical Co.,LTD | 24 | 36.94 | 12.34 |
| 39 | Manidip | g | 20mg | Nichi-Iko Pharmaceutical Co., Ltd. | 20 | 19.68 | 8.7 |
| 40 | Manidip | standard | 20mg | Nichi-Iko Pharmaceutical Co., Ltd. | 20 | 20.28 | 10.41 |
| 43 | Canselin | g | 20mg | Taiyo Pharmaceutical Industry Co., Ltd | 40 | 30.11 | 17.96 |
| 44 | Canselin | standard | 20mg | Taiyo Pharmaceutical Industry Co., Ltd | 40 | 34.6 | 32.91 |

FIG. 11

BIOEQUIVALENCE EVALUATION METHOD OF EVALUATING BIOEQUIVALENCE OF A GENERIC DRUG TO THE CORRESPONDING ORIGINAL DRUG

TECHNICAL FIELD

This invention relates to a bioequivalence evaluation method of evaluating bioequivalence of a generic drug to the corresponding original drug.

As an enormous sum of money and time are required to develop a new drug (an original drug) in the pharmaceutical industry, a company developing a new drug (an original drug) aims to recover the expenses spent for the development by acquiring a patent right with respect to the developed new drug and by exclusively manufacturing and selling the new drug. Once the term of existence of the patent right of the new drug has elapsed, other companies (generic drug makers) come to be able to manufacture and sell a drug having a chief ingredient almost identical to that of the corresponding original drug (a corresponding generic drug) without any restriction by the patent. Accordingly, after the term of existence of the patent right is over, the original drug and corresponding generic drugs are concurrently available on the market.

As a generic drug needs less development expenses in comparison with those needed by the corresponding original drug and the approval procedure for a generic drug with the Japanese Ministry of Health, Labour and Welfare, for example, is extremely easy compared with that for the corresponding original drug, generic drugs have a merit in supply thereof at a reasonable price. In recent years, the Japanese Ministry of Health, Labour and Welfare is taking measures to recommend the use of generic drugs as a part of the policy for suppression of medical expenses.

However, the reality is that the quantities of generic drugs consumed have not yet reached the level the Japanese Ministry of Health, Labour and Welfare expects. Therefore, measures for recommendation of further use of generic drugs are expected to be taken.

One of the reasons why an original drug is preferred to corresponding generic drugs which are available at a reasonable price is that people concerned with medical treatment doubt whether properties of generic drugs exhibited to living things are truly equivalent to those of the corresponding original drug exhibited to living things.

The examination for approval of a generic drug by the Japanese Ministry of Health, Labour and Welfare is focused on confirmation of equivalence of the generic drug to the corresponding original drug and bioequivalence is judged by the following method.

Figure 9:
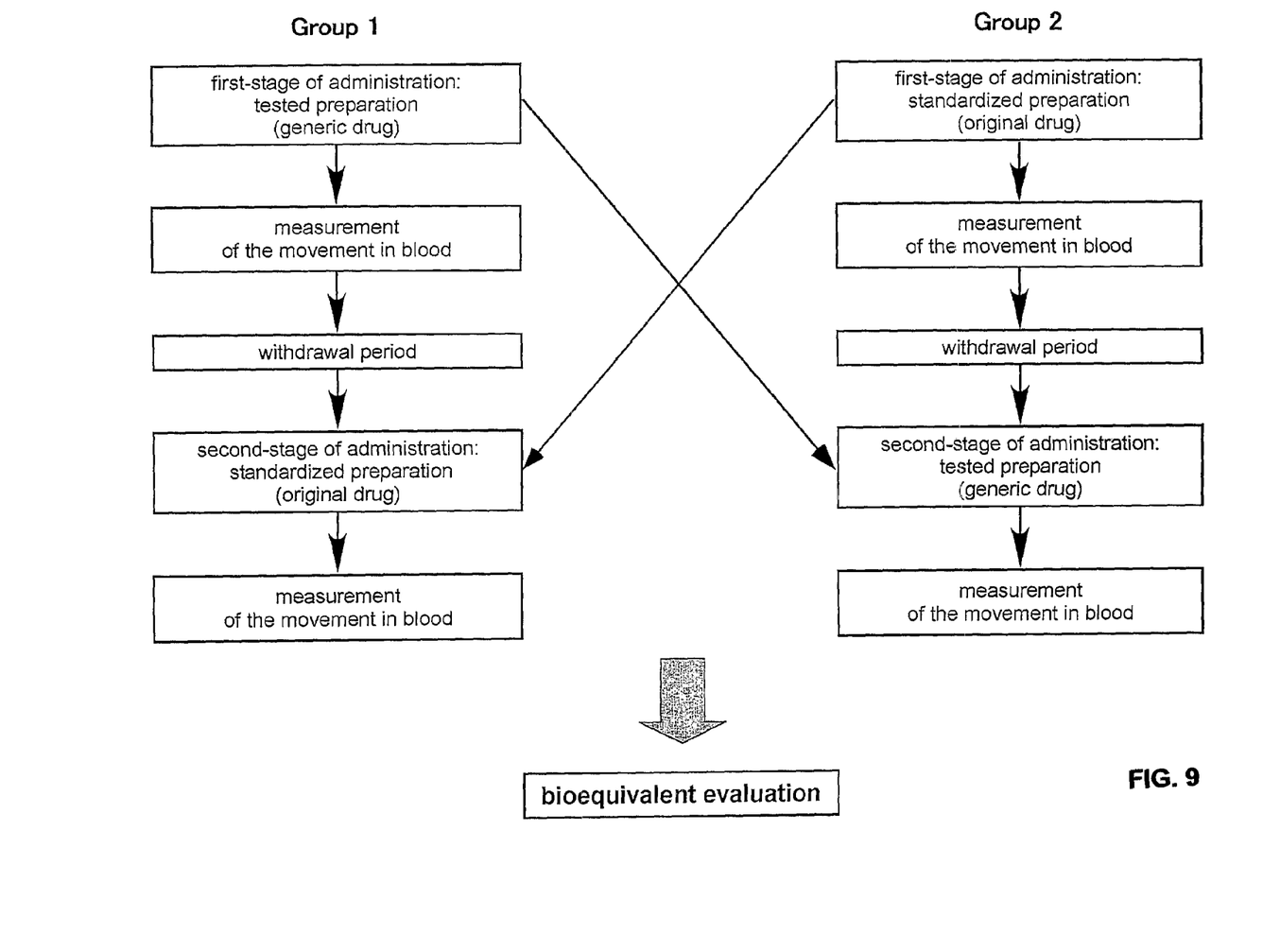
FIG. 9 is a drawing showing the method of a cross-over examination.

Firstly, healthy adult volunteers are employed as subjects (usually 12-24 persons) and divided into two groups (Group 1 and Group 2) in order to carry out a cross-over examination. The reason why patients are not employed as subjects is that blood concentration varies depending upon the state of illness and the physiological function of the patients as well as ages thereof. As shown in FIG. 9, an original drug is administered to Group 1 and the movement in blood of a non-metabolism drug and active metabolites are measured. After the fixed withdrawal period, a corresponding generic drug is administered and the movement in blood is measured in a similar manner. On the other hand, the generic drug is administered to Group 2 and the movement in blood of a non-metabolism drug and active metabolites are measured. After the fixed withdrawal period, the original drug is administered and the movement in blood is measured in a similar manner.

Figure 10:
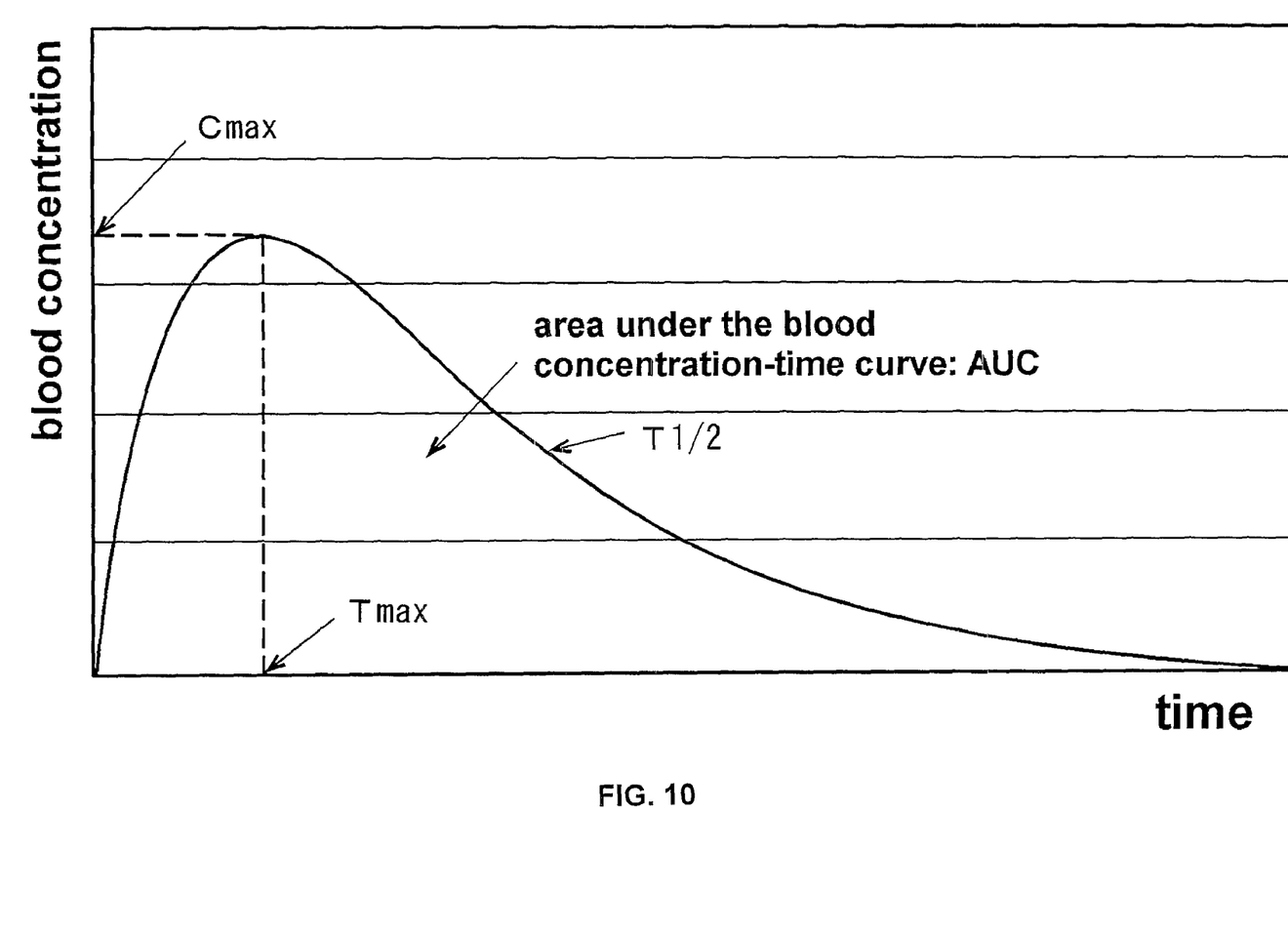
FIG. 10 is a graph showing the relationship between the blood concentration and time of an administered drug.

Then, as shown in FIG. 10, the blood concentration and time of the administered drugs are measured to obtain the maximum blood concentration (Cmax), the time-to-maximum blood concentration (Tmax), the half-life ($T_{1/2}$) or the mean residence time (MRT), and the blood concentration-area under the curve (AUC). Incidentally, the measures are taken not to give an approval to a generic drug having an average value of Cmax and AUC beyond the scope of between 80% and 125% for 90% confidence interval of the corresponding original drug.

However, even if bioequivalence of a generic drug is approved, releasing rate or the like of the chief ingredient thereof sometimes differs due to the differences of the dosage form and additives including excipients because such dosage form and additives are not regulated. Therefore, sufficient information has been accumulated on the effectiveness and safety of an original drug, while it is not always affirmed that there are no problems in the effectiveness and safety of a corresponding generic drug. Since the differences in quality of various kinds of additives and capsules or in tabletization techniques or the like cause differences in the absorption rate and time of a chief ingredient, which sometimes causes a difference in the drug effect (for example, Patent Publication 1), and since examination items of a generic drug on application for approval are fewer than those of the corresponding original drug because of exemption of a toxic examination and the like, high possibility of impurity contamination is sometimes pointed out. Accordingly, patients are forced to bear risks in exchange for the merit of reasonable price.

The above-mentioned problem in judgment of bioequivalence is not limited in Japan but is common all over the world. Accordingly, establishment of an accurate judgment technique of bioequivalence has been longed for.

Patent Publication 1: Japanese Patent Application KOKAI Publication No. 2000-1442

DISCLOSURE OF THE INVENTION

In order to solve the conventional problem mentioned above, it is necessary to make a comparison between generic drugs from the aspect of bioequivalence in order to determine which one is the most appropriate.

In the conventional bioequivalence test mentioned above, it is possible to make a comparison between an original drug and a corresponding generic drug, but it is not possible simply to make a comparison between generic drugs. That is because of the following reason.

As shown in FIG. 9, in the conventional bioequivalence test, subjects are divided into 2 groups. Each group takes both an original drug and a corresponding generic drug at a different time. And then the in vivo movement of each drug is measured. In the comparison between an original drug and a corresponding generic drug, each maker employs identical subjects for judgment of bioequivalence. Even if generic drugs are of the same kind, subjects vary from maker to maker. For this reason, it is possible to compare the test data between an original drug and a corresponding generic drug, but it is not possible simply to compare the data with those of other makers.

Figure 11:
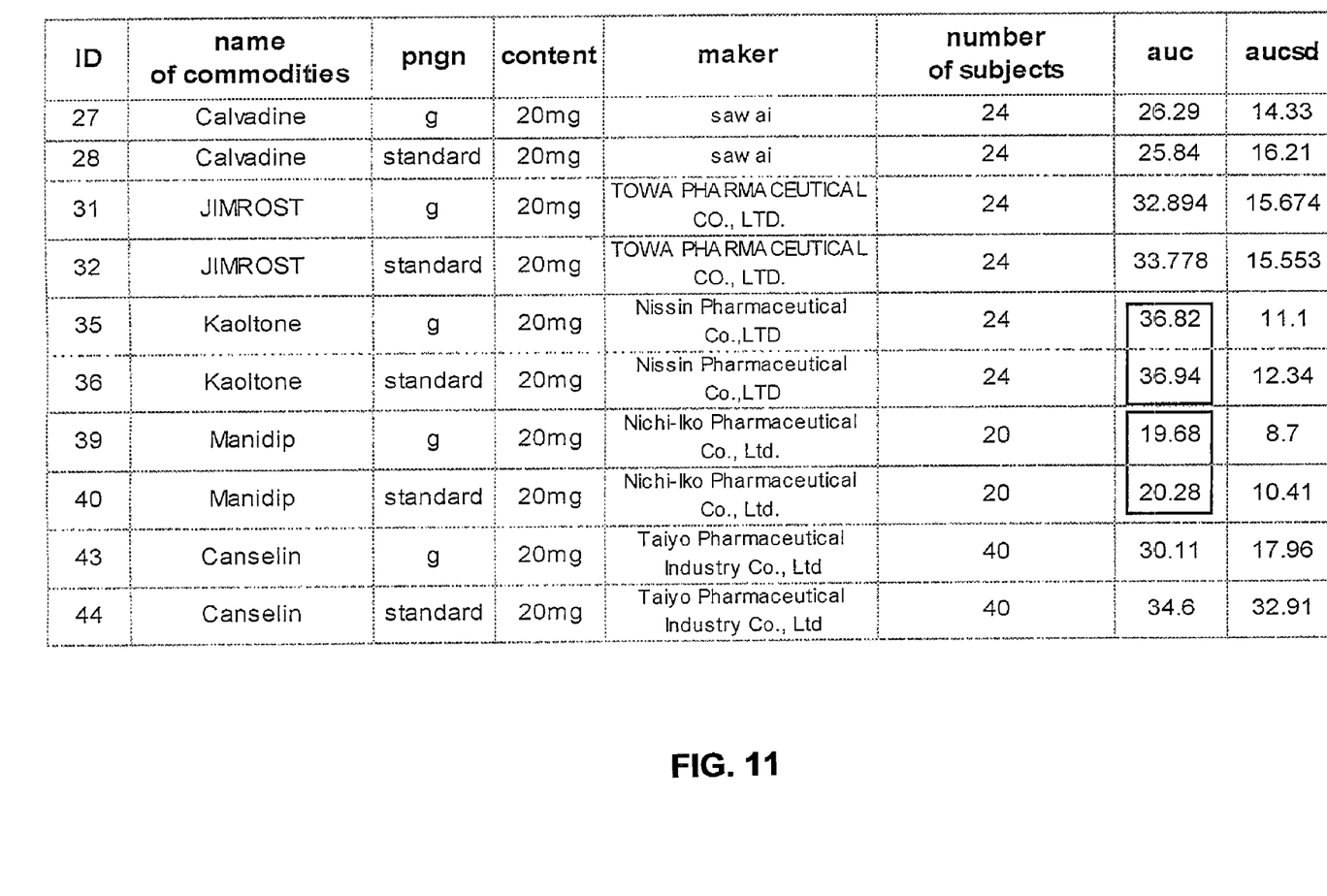
FIG. 11 is an example data of a plurality of generic drugs each bioequivalence of which is approved by the Japanese Ministry of Health, Labour and Welfare.

For example, data of a plurality of generic drugs, each bioequivalence of which is approved by the Japanese Ministry of Health, Labour and Welfare, are listed in FIG. 11. In a simple comparison between kaoltone (registered trade mark) and manidip (registered trade mark), the AUC for 20 mg of kaoltone (registered trade mark) is 36.82 and the AUC for 20 mg of manidip (registered trade mark) is 19.68. However, even in the case of taking a drug containing 20 mg of the identical ingredient (manidipine hydrochloride), each AUC differs surprisingly by 1.8 times. Nevertheless, both drugs have been approved as generic drugs through bioequivalence test. That is, requirements for approval of a generic drug in terms of the bioequivalence test should be always considered in comparison with those for approval of the corresponding original drug because the bioequivalence test requires a comparison of the generic drug with the corresponding original drug as to in vivo movement and therefore, it is difficult to have a discussion solely by drawing individual data. The problem exists not only in Japan, but also in the United States of America and European countries imposing similar approval requirements.

The problem has not been pointed out so far. Accordingly, it is the inventor of this application who has found the problem for the first time. The invention of this application has been made in consideration of the problem. Therefore, the problems to be solved by the invention are not only evaluation of bioequivalence of a generic drug in comparison with the corresponding original drug, but also presentation of a bioequivalence evaluation method capable of comparison between generic drugs.

The inventor of this application has studied on whether or not the coefficient of variation (CV) is available in order to compare bioequivalence between generic drugs. The coefficient of variation (CV) stands for the value obtained by dividing the standard deviation (SD) by the average value. It is also considered that judgment of bioequivalence is made by using the CV value because it is generally considered that the smaller the CV is, the more stable the quality is. However, in the case of a small number of subjects (12-24 subjects according to bioequivalent evaluation of the Japanese Ministry of Health, Labour and Welfare), a comparison is unable to be made solely by using the coefficient of variation of a generic drug because the coefficient of variation of an identical original drug (CVs) varies by each data of corresponding generic drugs due to the difference in subjects or the like.

The inventor of this application has found that it is possible to compare bioequivalence between generic drugs by introducing the concept of the calibration coefficient of variation (CCV) which is the value obtained by dividing further the coefficient of variation (CV) of a generic drug by the coefficient of variation of the corresponding original drug (CVs). Namely, it is possible to compare bioequivalence between generic drugs by comparing the CCV between generic drugs. In this way the inventor of this application has come to complete the invention of this application.

Namely, a bioequivalence evaluation method of this invention is a bioequivalence evaluation method of evaluating bioequivalence of a generic drug to the corresponding original drug, characterized in that, in the case of administration of the original drug and the generic drug (both mentioned above), each coefficient of variation (CV) is obtained by dividing by the average value each standard deviation (SD) of at least one kind of data of in vivo movement indices numerically evaluating the properties of each drug with respect to in vivo movement thereof, and the calibration coefficient of variation (CCV) is obtained by dividing the coefficient of variation (CV) by the coefficient of variation of the original drug (CVs), and then bioequivalence is evaluated by means of the calibration coefficient of variation (CCV).

In the bioequivalence evaluation method of this invention, the concept of the calibration coefficient of variation (CCV) which is the value obtained by dividing the coefficient of variation (CV) of a generic drug by the coefficient of variation of the corresponding original drug (CVs) is introduced, and bioequivalence between generic drugs is evaluated by using the values. As the concept of the calibration coefficient of variation (CCV) is the value used for judging the degree of variation of data of in vivo movement indices of a generic drug in comparison with the degree of variation of the data of in vivo movement indices of the corresponding original drug, a comparison with the corresponding original drug is always taken into consideration. For this reason, in the case of bioequivalence evaluation between generic drugs, a comparison is able to be made easily because the situation of different subjects is covered.

As a parameter for comparison, concretely, G value as shown in the following expression can be used. The value underneath the square root sign of the numerator in the Expression (1) is the value obtained by squaring a certain calibration coefficient of variation. The denominator is one because a certain calibration coefficient of variation of an original drug underneath the square root sign of the denominator is one due to (CVs/(CVs). The G value thus calculated helps to judge the degree of the difference from the degree of variation of the corresponding original drug. In the case that the degree of variation is identical between the original drug and the generic drug, The G value equals one. That is, the nearer one the G value is, the more excellent the bioequivalence is judged to be.

[Expression (1)]

$$G = \frac{\sqrt{(CCV_g)^2}}{\sqrt{(CCV_s)^2}} \quad (1)$$

In this application, in vivo movement indices stand for any and all numerically evaluating the properties of a drug with respect to the in vivo movement. Concretely, as to internal medicines, for example, the maximum blood concentration (Cmax), the time-to-maximum blood concentration (Tmax), the half-life ($T_{1/2}$), the mean residence time (MRT), the blood concentration-area under the curve (AUC), and the relative absorption rate (F) and the like after administration are cited. As to plasters and pressure sensitive adhesives, the maximum blood concentration (Cmax), the time-to-maximum blood concentration (Tmax), the blood concentration-area under the curve (AUC), and the relative absorption rate (F) and the like after transdermal administration are cited. Since these in vivo movement indices are contained in the bioequivalence data of the conventional generic drugs to be filed for approval, the indices can be introduced from the existing data published by each pharmaceutical maker at its website or the like instead of measuring the data again.

In the bioequivalence evaluation method of this invention, bioequivalence is preferably evaluated by using four kinds of calibration coefficients of variation, namely, the calibration coefficient of variation of the maximum blood concentration (Cmax), the calibration coefficient of variation of the time-to-maximum blood concentration (Tmax), the calibration coefficient of variation of the half-life (T1/2) or the mean residence time (MRT), and the calibration coefficient of variation of the blood concentration-area under the curve (AUC) or the relative absorption rate (F). More accurate judgment of bioequivalence can be made by using all these four kinds of the calibration coefficients of variation. These are expressed by combination of four kinds of calibration coefficients of variation, and visual judgment can be made through graphing.

Further, as a method of judging bioequivalence, bioequivalence can also be evaluated according to the following Expression (2) wherein CCVcmax g stands for the calibration coefficient of variation of Cmax (the maximum blood concentration) of a generic drug under a fasting condition, $CCV_T$max g stands for the calibration coefficient of variation of Tmax (the time-to-maximum blood concentration) of the generic drug under the fasting condition, $CCV_{T1/2}$ g stands for the calibration coefficient of variation of $T_{1/2}$ (the half-life) of the generic drug under the fasting condition, and $CCV_{AUC}$ g stands for the calibration coefficient of variation of AUC (the blood concentration-area under the curve) of the generic drug under the fasting condition, and wherein CCVcmax s stands for the calibration coefficient of variation of Cmax (the maximum blood concentration) of the corresponding original drug under the fasting condition, $CCV_T$max s stands for the calibration coefficient of variation of Tmax (the time-to-maximum blood concentration) of the original drug under the fasting condition, $CCV_{T1/2}$ s stands for the calibration coefficient of variation of $T_{1/2}$ (the half-life) of the original drug under the fasting condition, and $CCV_{AUC}$ s stands for the calibration coefficient of variation of AUC (the blood concentration-area under the curve) of the original drug under the fasting condition.

[Expression (2)]

$$G = \frac{\sqrt{(CCV_{Cmaxg})^2 + (CCV_{Tmaxg})^2 + (CCV_{t1/2g})^2 + (CCV_{AUCg})^2}}{\sqrt{(CCV_{Cmaxs})^2 + (CCV_{Tmaxs})^2 + (CCV_{t1/2s})^2 + (CCV_{AUCs})^2}} \quad (2)$$

The value underneath the square root sign of the numerator in the Expression (2) is the value obtained by totaling the squared value of each of the calibration coefficients of variation of a generic drug. And the denominator is two because each of the calibration coefficients of variation of the corresponding original drug underneath the square root sign of the denominator is one due to CVs/CVs and then the total figure underneath the square root sign is four. The G value thus calculated helps to judge the degree of the difference from the degree of variation of the corresponding original drug. In the case that the degree of variation is identical between the original drug and a corresponding generic drug, the G value equals one. That is, the nearer one the G value is, the more excellent the bioequivalence is judged to be. MRT (mean residence time) may be used in place of T1/2 (half-life). As to a drug combined with a plurality of active ingredients (what is called "combination drug"), bioequivalence can be evaluated by the total figure obtained by calculating the G value of each active ingredient and further by totaling the G values. Further, as shown in the following Expression (3), a comparison can be made after multiplying a square of each of the calibration coefficients of variation by a weighting factor ($\alpha$, $\beta$, $\gamma$, $\delta$). In the case that different contribution to bioequivalence is expected depending on the kind of variation coefficient, more appropriate judgment can be made in consideration of the different contribution.

[Expression (3)]

$$G = \frac{\sqrt{\alpha(CCV_{Cmaxg})^2 + \beta(CCV_{Tmaxg})^2 + \gamma(CCV_{t1/2g})^2 + \delta(CCV_{AUCg})^2}}{\sqrt{\alpha(CCV_{Cmaxs})^2 + \beta(CCV_{Tmaxs})^2 + \gamma(CCV_{t1/2s})^2 + \delta(CCV_{AUCs})^2}} \quad (3)$$

In the case that there are two conditions for a bioequivalence test of a drug (for example, in the case that, with respect to bioequivalence test of the Japanese Ministry of Health, Labour and Welfare, data are collected for subjects both under a fasting condition and during eating and drinking), bioequivalence can be evaluated in the following manner. Namely, the method is a bioequivalence evaluation method of evaluating bioequivalence, characterized in that, in the case that there are two evaluation conditions that are Condition 1 and Condition 2, bioequivalence is evaluated according to the following Expression (4) wherein CCVcmax gbm stands for the calibration coefficient of variation of Cmax (the maximum blood concentration) of a generic drug under the Condition 1, $CCV_T$max gbm stands for the calibration coefficient of variation of Tmax (the time-to-maximum blood concentration) of the generic drug under the Condition 1, $CCVt_{1/2}$ gbm stands for the calibration coefficient of variation of T1/2 (the half-life) of the generic drug under the Condition 1, $CCV_A$uc gbm stands for the calibration coefficient of variation of AUC (the blood concentration-area under the curve) of the generic drug under the Condition 1, CCVcmax gam stands for the calibration coefficient of variation of Cmax (the maximum blood concentration) of the generic drug under the Condition 2, $CCV_T$max gam stands for the calibration coefficient of variation of Tmax (the time-to-maximum blood concentration) of the generic drug under the Condition 2, $CCVt_{1/2\ gam}$ stands for the calibration coefficient of variation of T1/2 (the half-life) of the generic drug under the Condition 2, $CCV_{AUC}$ gam stands for the calibration coefficient of variation of AUC (the blood concentration-area under the curve) of the generic drug under the Condition 2, and wherein CCVcmax sbm stands for the calibration coefficient of variation of Cmax (the maximum blood concentration) of the corresponding original drug under the Condition 1, $CCV_T$max sbm stands for the calibration coefficient of variation of Tmax (the time-to-maximum blood concentration) of the original drug under the Condition 1, $CCVt_{1/2}$ sbm stands for the calibration coefficient of variation of T1/2 (the half-life) of the original drug under the Condition 1, $CCV_{AUC}$ sbm stands for the calibration coefficient of variation of AUC (the blood concentration-area under the curve) of the original drug under the Condition 1, CCVcmax sam stands for the calibration coefficient of variation of Cmax (the maximum blood concentration) of the original drug under the Condition 2, $CCV_T$max sam stands for the calibration coefficient of variation of Tmax (the time-to-maximum blood concentration) of the original drug under the Condition 2, $CCV_{T1/2}$ sam stands for the calibration coefficient of variation of T1/2 (the half-life) of the original drug under the Condition 2, $CCV_{AUC}$ sam stands for the calibration coefficient of variation of AUC (the blood concentration-area under the curve) of the original drug under the Condition 2.

[Expression (4)]

$$G = \frac{\sqrt{(CCV_{Cmaxgbm})^2 + (CCV_{Tmaxgbm})^2 + (CCV_{t1/2gbm})^2 + (CCV_{AUCgbm})^2} + \sqrt{(CCV_{Cmaxgam})^2 + (CCV_{Tmaxgam})^2 + (CCV_{t1/2gam})^2 + (CCV_{AUCgam})^2}}{\sqrt{(CCV_{Cmaxsbm})^2 + (CCV_{Tmaxsbm})^2 + (CCV_{t1/2sbm})^2 + (CCV_{AUCsbm})^2} + \sqrt{(CCV_{Cmaxsam})^2 + (CCV_{Tmaxsam})^2 + (CCV_{t1/2sam})^2 + (CCV_{AUCsam})^2}} \quad (4)$$

The denominator is four because each of the calibration coefficients of variation of an original drug underneath the square root sign of the denominator is one due to CVs/CVs. The G value thus calculated helps to judge the degree of the difference from the degree of variation of the original drug. In the case that the degree of variation is the same between the original drug and a corresponding generic drug, The G value equals one. That is, the nearer one the G value is, the more excellent the bioequivalence is judged to be. MRT (mean residence time) may be used in place of $T_{1/2}$ (half-life).

In this way, in the case that there are two conditions for a bioequivalence test of a drug, bioequivalence can be evaluated by obtaining the calibration coefficient of variation with respect to each condition, Condition 1 and Condition 2, and then by using the G value shown in the above-mentioned Expression (4). Even in the case that there are two conditions, bioequivalence can be judged by using the calibration coefficient of variation solely under the Condition 1 or the Condition 2, together with or without the G value obtained according to the above-mentioned Expression (2).

Another aspect of this invention is defined as follows. That is, a bioequivalence evaluation system for evaluating bioequivalence of a generic drug to the corresponding original drug, characterized in that, in the case of administration of the original drug and the generic drug, the bioequivalence evaluation system is provided with:
(a) a calibration coefficient of variation memorizing means of memorizing data of the calibration coefficient of variation (CCV) which is obtained by dividing by the average value the standard deviation (SD) of at least one kind of data selected from the group consisting of the maximum blood concentration (Cmax), the time-to-maximum blood concentration (Tmax), the half-life (T1/2), the mean residence time (MRT), the blood concentration-area under the curve (AUC) and the relative absorption rate (F) after administration to obtain each of the variation coefficients (CV) and further by dividing the variation coefficient (CV) by the variation coefficient of the original drug (CVs);
(b) a selecting means of selecting data concerning the original drug from the calibration coefficient of variation memorizing means; and
(c) an outputting means of outputting the data selected by the selecting means.

According to such bioequivalence evaluation system, with respect to an optional original drug selected by the selecting means, the calibration coefficient of variation of a corresponding generic drug is output by means of the outputting means, and then, a comparison can be made with respect to the calibration coefficients of variation of each of generic drugs. Accordingly, a comparison of bioequivalence can be made between generic drugs.

Another aspect of this invention is defined as follows. That is, a program for evaluating bioequivalence of a generic drug to the corresponding original drug and for enabling a computer to carry out the following means:

(a) a calibration coefficient of variation memorizing means of memorizing data of the calibration coefficient of variation (CCV) which is obtained by dividing by the average value the standard deviation (SD) of at least one kind of data selected from the group consisting of the maximum blood concentration (Cmax), the time-to-maximum blood concentration (Tmax), the half-life (T1/2), the mean residence time (MRT), the blood concentration-area under the curve (AUC) and the relative absorption rate (F) after administration in the case of administration of the original drug and the generic drug to obtain each of the variation coefficients (CV) and further by dividing the variation coefficient (CV) by the variation coefficient (CVs) of the original drug;
(b) a selecting means of selecting data concerning the original drug from the calibration coefficient of variation memorizing means; and
(c) an outputting means of outputting the data selected by the selecting means.

According to the program thus defined, by installing the program on a computer, actions and effects similar to those of bioequivalence evaluation system are obtained.

DESCRIPTION OF REFERENCE NUMERALS

1 . . . Bioequivalence evaluation system
11 . . . Controlling part
11a . . . CPU 14 ... Memorizing part (14a ... memory area of evaluation program, 14b ... memory area of drug data)
12 ... Inputting part
13 ... Displaying part
15 ... Outputting part

BEST MODE OF CARRYING OUT THE INVENTION

In the bioequivalence evaluation system of this invention, firstly, data of the maximum blood concentration (Cmax), the time-to-maximum blood concentration (Tmax), the half-life (T1/2) or the mean residence time (MRT), and the blood concentration-area under the curve (AUC) or the relative absorption rate (F) after administration in the case of administration of an original drug and a corresponding generic drug are arranged. These data can be introduced with ease from the existing data (such data is described in what is called "orange book" in Japan)

Then, the standard deviation (SD) is calculated from each of these data, and each variation coefficient (CV) is obtained by dividing the standard deviation (SD) by the average value, and further the calibration coefficient of variation (CCV) is obtained by dividing the variation coefficient (CV) by the variation coefficient of the original drug (CVs). Accordingly, as to the original drug as a standard, the calibration coefficient of variation (CCV) is one. As the calibration coefficient of variation of a corresponding generic drug comes near to one, the generic drug comes to be judged to be more bioequivalent.

Hereunder, as to bioequivalence evaluation method of this invention, an explanation is made by citing manidipine hydrochloride, a hypotensive drug lowering the blood pressure.

There exists Calslot (Takeda Yakuhin Kogyo Kabushiki Kaisha's registered trademark) which is an original drug containing manidipine hydrochloride as an active ingredient. Among corresponding generic drugs are Kaoltone (Nissin Pharmaceutical Co., LTD.'s registered trademark), Manidip (Nichi-iko Pharmaceutical Co., LTD.'s registered trademark) and Canselin (Taiyo Yakuhin Co., LTD.'s registered trademark). In the data of these drugs with respect to bioequivalence submitted to the Japanese Ministry of Health, Labour and Welfare, the maximum blood concentration (Cmax), the time-to-maximum blood concentration (Tmax), the half-life (T1/2) and the blood concentration-area under the curve (AUC) are described. Then, from those values the standard deviation (SD) is calculated and the standard deviation (SD) is divided by the average value to obtain each of the variation coefficients (see Table 1).

TABLE 1

| name of commodity | pngn | content | nonproprietary name | name of original drug | number of subjects | AUC | AUCsd | Cmax | Cmaxsd | Tmax | Tmaxsd | $T_{1/2}$ | $T_{1/2sd}$ | ad1 |
|---|---|---|---|---|---|---|---|---|---|---|---|---|---|---|
| Calvadine | g | 10 mg | manidipine hydrochloride | Calslot | 24 | 29.07 | 12.87 | 6.9 | 3.38 | 1.56 | 0.63 | 4.07 | 1.32 | lactose |
| Calvadine | standard | 10 mg | manidipine hydrochloride | Calslot | 24 | 30.88 | 12.88 | 7.44 | 3.12 | 1.42 | 0.52 | 4.74 | 1.82 | lactose |
| Calvadine | g | 20 mg | manidipine hydrochloride | Calslot | 24 | 26.29 | 14.33 | 5.7 | 3.38 | 1.96 | 0.86 | 4.55 | 2.39 | lactose |
| Calvadine | standard | 20 mg | manidipine hydrochloride | Calslot | 24 | 25.84 | 16.21 | 6.11 | 3.16 | 1.42 | 0.43 | 4.6 | 2.03 | lactose |
| JIMROST | g | 10 mg | manidipine hydrochloride | Calslot | 24 | 14.594 | 10.426 | 4.06 | 3.012 | 1.46 | 0.66 | 8.426 | 3.414 | lactose |
| JIMROST | standard | 10 mg | manidipine hydrochloride | Calslot | 24 | 13.176 | 9.722 | 3.913 | 2.859 | 1.33 | 0.64 | 9.401 | 4.832 | lactose |
| JIMROST | g | 20 mg | manidipine hydrochloride | Calslot | 24 | 32.894 | 15.674 | 8.556 | 4.259 | 1.85 | 1.27 | 8.364 | 2.512 | lactose |
| JIMROST | standard | 20 mg | manidipine hydrochloride | Calslot | 24 | 33.778 | 15.553 | 8.587 | 3.809 | 1.54 | 0.83 | 9.566 | 4.926 | lactose |
| Kaoltone | g | 10 mg | manidipine hydrochloride | Calslot | 24 | 19.82 | 7.39 | 4.84 | 1.25 | 1.54 | 0.33 | 3.21 | 1.05 | lactose |
| Kaoltone | standard | 10 mg | manidipine hydrochloride | Calslot | 24 | 20.03 | 7.06 | 4.76 | 1.82 | 1.69 | 0.51 | 3.24 | 1.03 | lactose |
| Kaoltone | g | 20 mg | manidipine hydrochloride | Calslot | 24 | 36.82 | 11.1 | 11.96 | 4.82 | 1.73 | 0.51 | 2.29 | 0.48 | lactose |
| Kaoltone | standard | 20 mg | manidipine hydrochloride | Calslot | 24 | 36.94 | 12.34 | 12.03 | 4.33 | 1.45 | 0.41 | 2.39 | 1.03 | lactose |
| Manidip | g | 10 mg | manidipine hydrochloride | Calslot | 20 | 17.56 | 6.94 | 4.09 | 1.89 | 1.35 | 0.4 | 7.13 | 2.27 | lactose |
| Manidip | standard | 10 mg | manidipine hydrochloride | Calslot | 20 | 18.66 | 5.88 | 4.09 | 1.63 | 1.55 | 0.71 | 7.08 | 2.09 | lactose |
| Manidip | g | 20 mg | manidipine hydrochloride | Calslot | 20 | 19.68 | 8.7 | 4.41 | 2.51 | 1.3 | 0.38 | 7.1 | 2.06 | lactose |
| Manidip | standard | 20 mg | manidipine hydrochloride | Calslot | 20 | 20.28 | 10.41 | 4.41 | 2.34 | 1.45 | 0.32 | 6.67 | 1.97 | lactose |
| Canselin | g | 10 mg | manidipine hydrochloride | Calslot | 30 | 35.08 | 14.56 | 6.94 | 2.9 | 1.9 | 1.1 | 7.31 | 2.54 | lactose |
| Canselin | standard | 10 mg | manidipine hydrochloride | Calslot | 30 | 30.77 | 10.61 | 6.66 | 2.66 | 1.5 | 0.5 | 7.3 | 2.77 | lactose |
| Canselin | g | 20 mg | manidipine hydrochloride | Calslot | 40 | 30.11 | 17.96 | 5.43 | 3.53 | 1.6 | 0.8 | 8.06 | 2.06 | lactose |
| Canselin | standard | 20 mg | manidipine hydrochloride | Calslot | 40 | 34.6 | 32.91 | 5.78 | 3.66 | 1.7 | 1 | 7.62 | 1.74 | lactose |

Further, the calibration coefficient of variation (CCV) is obtained by dividing the variation coefficient (CV) by the variation coefficient of the original drug (CVs). Each data with respect to 20 mg content tablet thus calculated is shown in FIG. 1 wherein auccv stands for the calibration coefficient of variation of the blood concentration-area under the curve (AUC), cmaxccv stands for the calibration coefficient of variation of the maximum blood concentration (Cmax), tmaxccv stands for the calibration coefficient of variation of the time-to-maximum blood concentration (Tmax), thccv stands for the calibration coefficient of variation of the half-life (T1/2).

Figure 1:
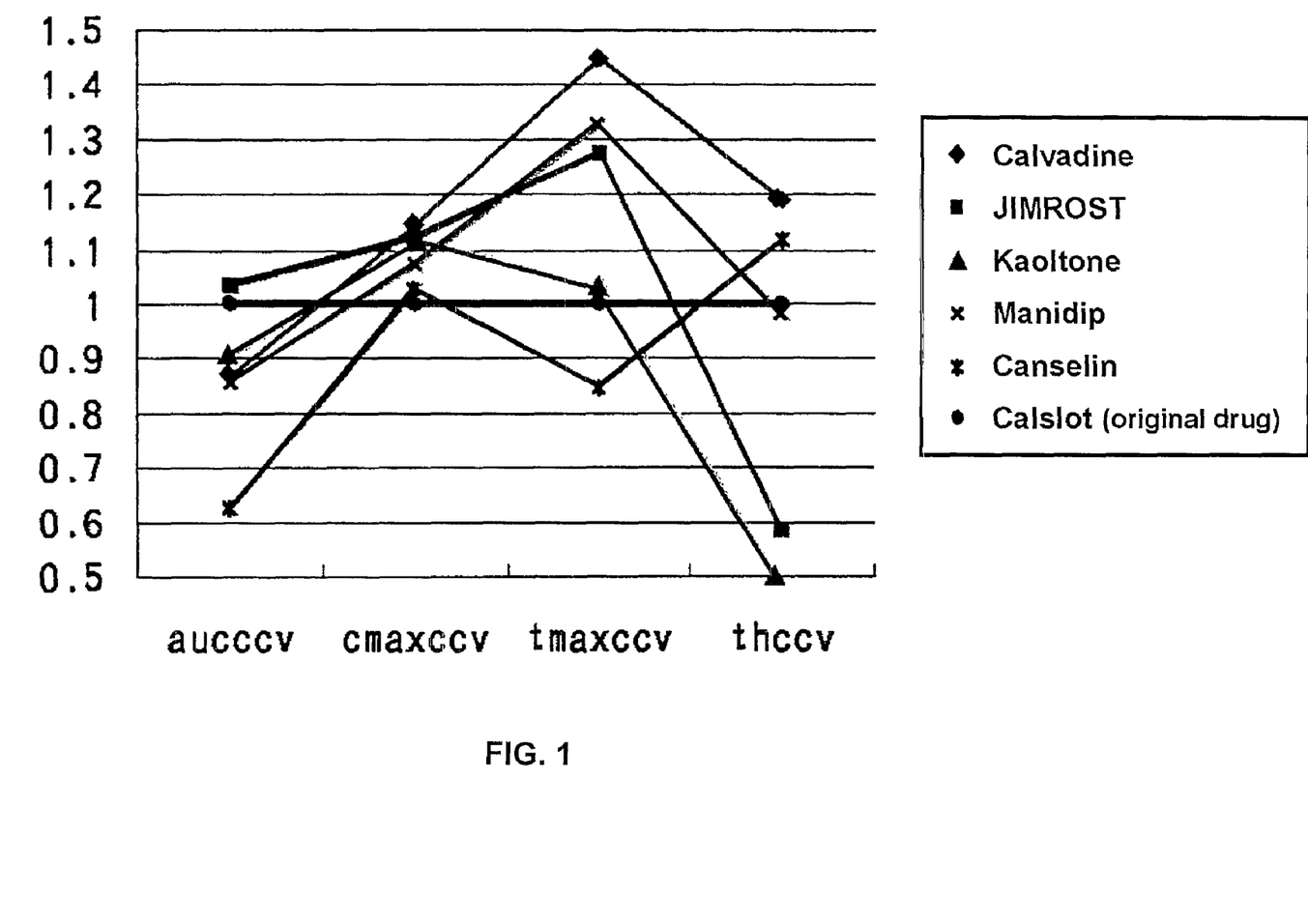
FIG. 1 is data on each of the calibration coefficients of variation (CCV) with respect to a tablet containing 20 mg of an original drug and a tablet containing 20 mg of a corresponding generic drug.

In FIG. 1, with respect to Calslot (registered trademark) which is an original drug, every of the values is one. And then, it is possible to compare bioequivalence between generic drugs on the basis of the degree of difference of each generic drug from one. In the case of comparing the values of AUC between Kaoltone (registered trademark) and Manidip (registered trademark), the former's value is 36.82 and the latter's value is 19.68, which seemingly shows large difference. However, in the case of comparison by using auccv, the former's value is 0.9 and the latter's value is 0.85, which does not show such large difference.

In the case of a generic drug, the time for AUC sometimes varies because the time for AUC can be defined optionally as the time necessary for the drug to exhibit the properties thereof as far as it is based on fact. However, since the calibration coefficient of variation (CCV) is calculated on the basis of AUCs the times for which are identical and therefore the condition is identical between the original drug and the generic drug, the above-mentioned values calculated according to the Expression (2) or Expression (4) does not come into question, even if the time for AUC varies by makers. Since the blood concentration of a drug nears zero as time elapses and the time for AUC is defined as the time necessary for the drug to exhibit properties thereof, even if the time for AUC is infinite, it is considered that such contribution to values is small and therefore almost the same values are obtained.

In the case that a drug is sustained release preparation, since data with respect to the bioequivalence test of the Japanese Ministry of Health, Labour and Welfare are collected from subjects both under a fasting condition and during eating and drinking, bioequivalence is preferably evaluated according to the following Expression (5) wherein CCVcmax gbm stands for the calibration coefficient of variation of Cmax (the maximum blood concentration) of a generic drug under a fasting condition, $CCV_T$max gbm stands for the calibration coefficient of variation of Tmax (the time-to-maximum blood concentration) of the generic drug under the fasting condition, $CCV_{MRT}$ gbm stands for the calibration coefficient of variation of MRT (the mean residence time) of the generic drug under the fasting condition, $CCV_{AUC}$ gbm stands for the calibration coefficient of variation of AUC (the blood concentration-area under the curve) of the generic drug under the fasting condition, CCVcmax gam stands for the calibration coefficient of variation of Cmax (the maximum blood concentration) of the generic drug during eating and drinking, $CCV_T$max gam stands for the calibration coefficient of variation of Tmax (the time-to-maximum blood concentration) of the generic drug during eating and drinking, $CCV_{MRT}$ gam stands for the calibration coefficient of variation of MRT (the mean residence time) of the generic drug during eating and drinking, $CCV_{AUC}$ gam stands for the calibration coefficient of variation of AUC (the blood concentration-area under the curve) of the generic drug during eating and drinking.

[Expression (5)]

$$G = \frac{\sqrt{(CCV_{Cmaxgbm})^2 + (CCV_{Tmaxgbm})^2 + (CCV_{t1/2gbm})^2 + (CCV_{AUCgbm})^2} + \sqrt{(CCV_{Cmaxgam})^2 + (CCV_{Tmaxgam})^2 + (CCV_{t1/2gam})^2 + (CCV_{AUCgam})^2}}{4} \quad (5)$$

Further, a square of each of the calibration coefficients of variation can be multiplied by a weighting factor ($\alpha$, $\beta$, $\gamma$, $\delta$). In the case that different contribution to bioequivalence is expected depending on the kind of variation coefficient, such weighting allows us to make more appropriate judgment in consideration of such different contribution.

<Bioequivalence Evaluation System>

On the basis of bioequivalence evaluation method of this invention, a database for an original drug and a corresponding generic drug is built in a computer and a system for searching bioequivalence evaluation can be constructed.

Figure 2:
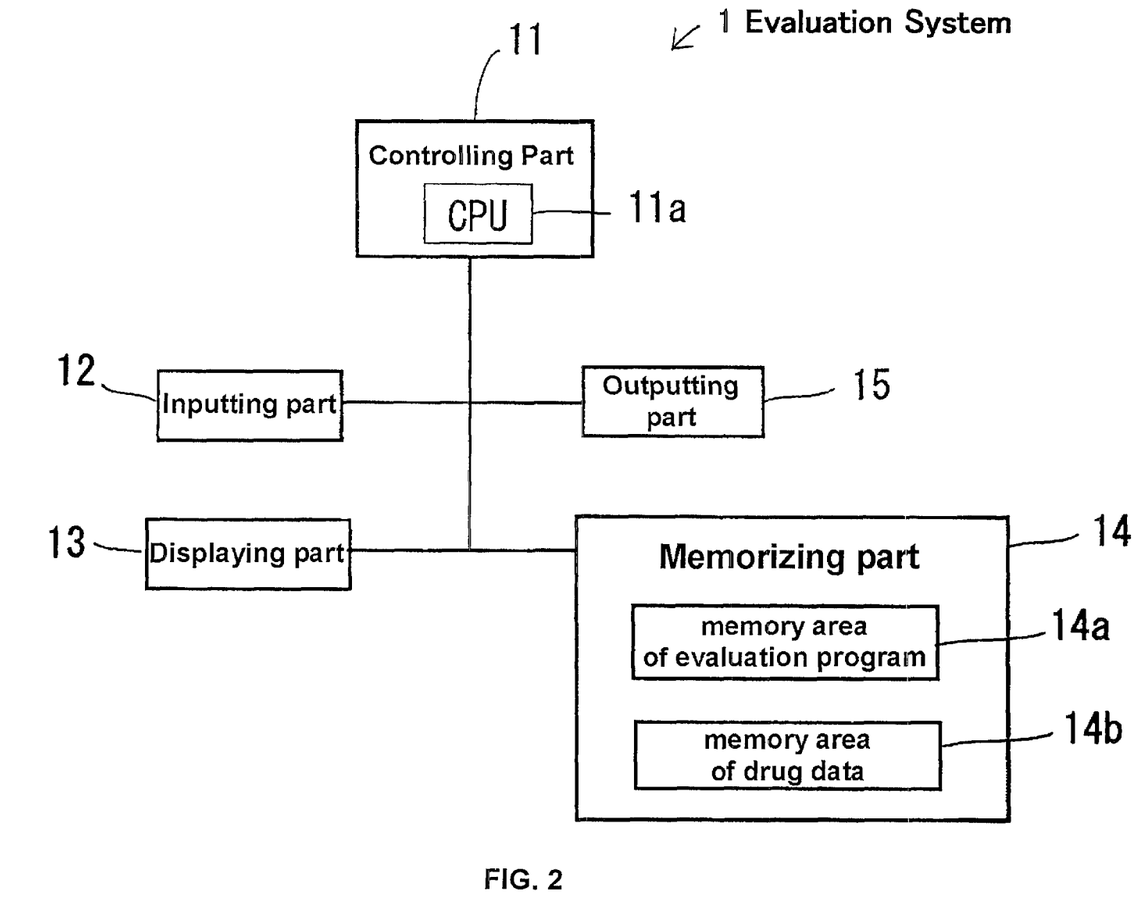
FIG. 2 is a block diagram of bioequivalence evaluation system in a working example.

The block diagram of such bioequivalence evaluation system is shown in FIG. 2. Bioequivalence Evaluation System 1 is provided with Controlling Part 11, Inputting Part 12, Displaying Part 13, Memorizing Part 14 and Outputting Part 15.

Controlling Part 11 is provided with CPU 11a and connected to each element which makes up Bioequivalence Evaluation System 1. CPU 11a controls each element by reading out from Memory Area of Evaluation Program 14a and carrying out a bioequivalence evaluation program. Inputting Part 12 is used for carrying out an inputting operation in Bioequivalence Evaluation System 1 and consists of a keyboard, a mouse and the like, which are not illustrated. Displaying Part 13 is used for displaying on a page selection of an original drug or a corresponding generic drug, in vivo movement data, CCV values, G values and the like, and consists of CRT and the like. Memorizing Part 14 is provided with Memory Area of Evaluation Program 14a and Memory Area of Drug Data 14b. Memory Area of Evaluation Program 14a is an area for memorizing bioequivalence evaluation program, and Memory Area of Drug Data 14b is an area for calculating the maximum blood concentration (Cmax), the time-to-maximum blood concentration (Tmax), the half-life ($T_{1/2}$), the mean residence time (MRT), the blood concentration-area under the curve (AUC), each of standard deviations (SD) and each variation coefficient (CV), and for memorizing the variation coefficient (CV), each of the calibration coefficients of variation (CCV) and the like.

Figure 3:
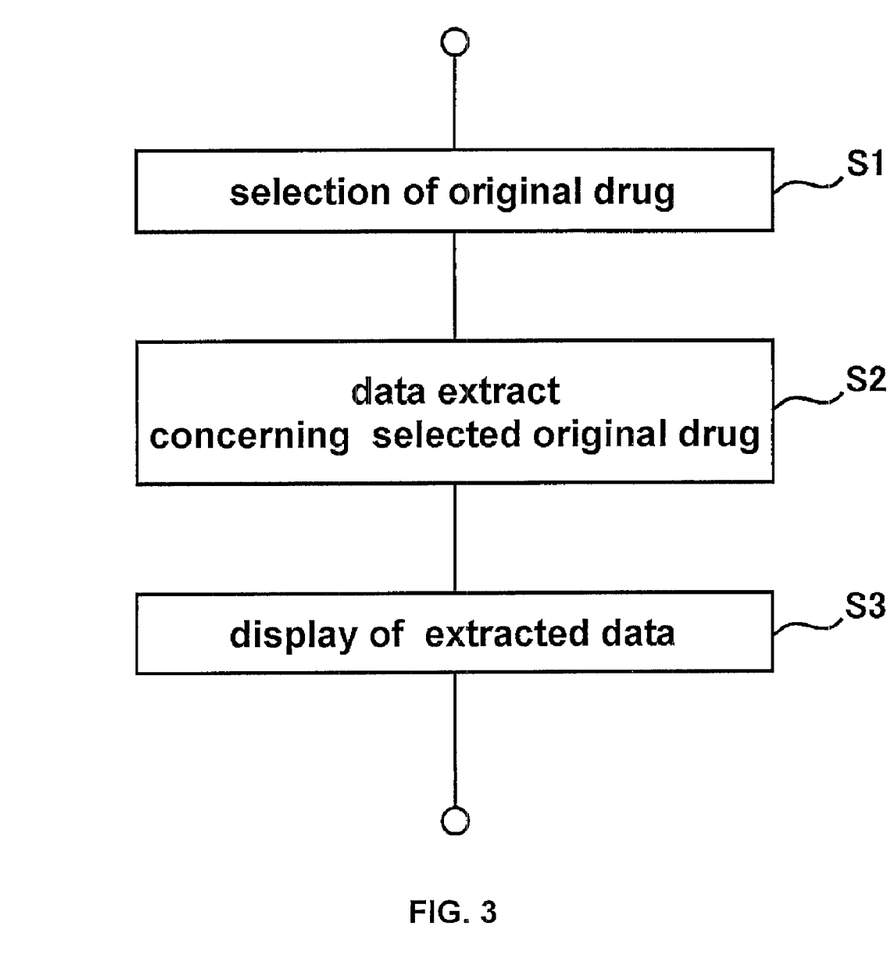
FIG. 3 is a flow chart of bioequivalence evaluation system in a working example.
Figure 4:
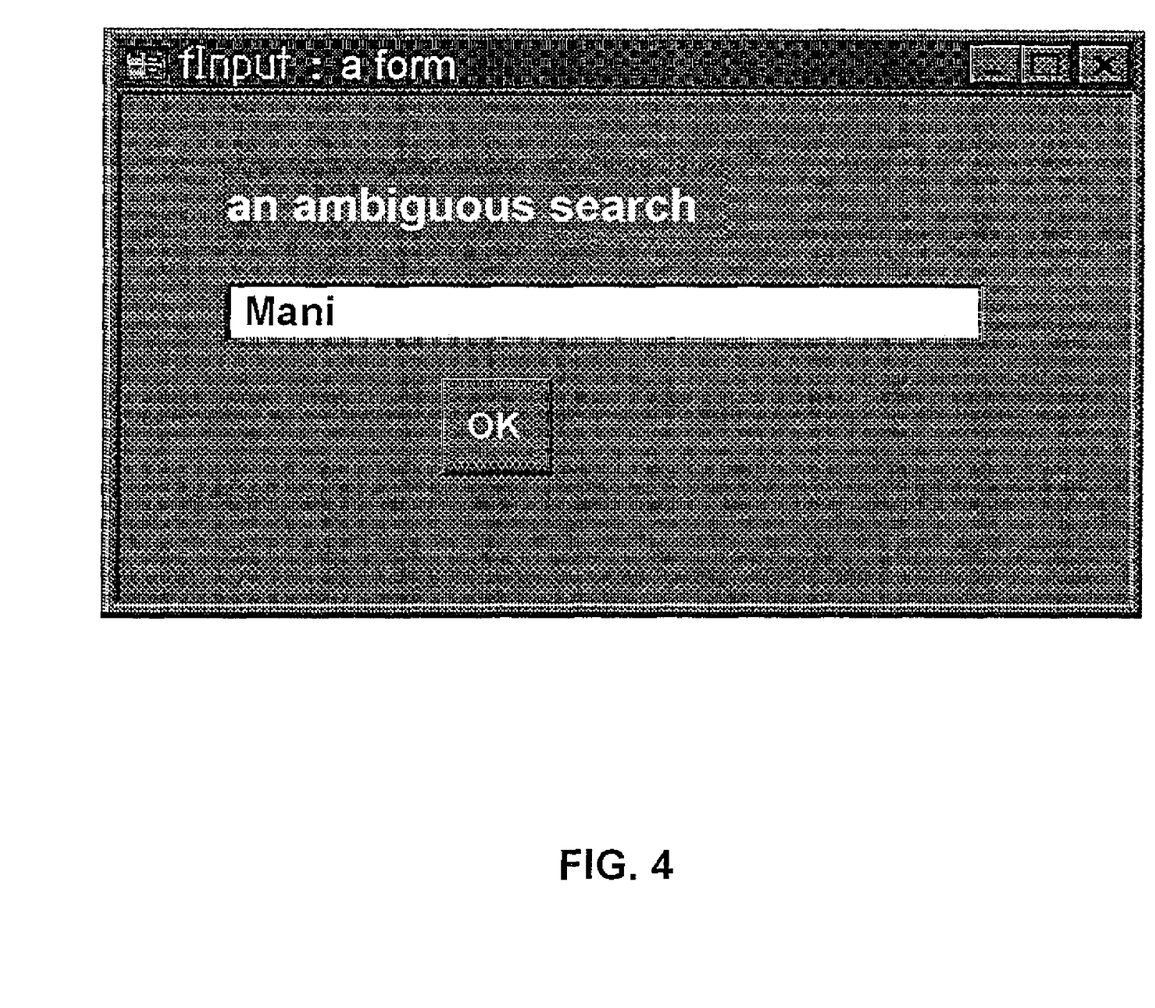
FIG. 4 is an ambiguous search page.
Figure 5:
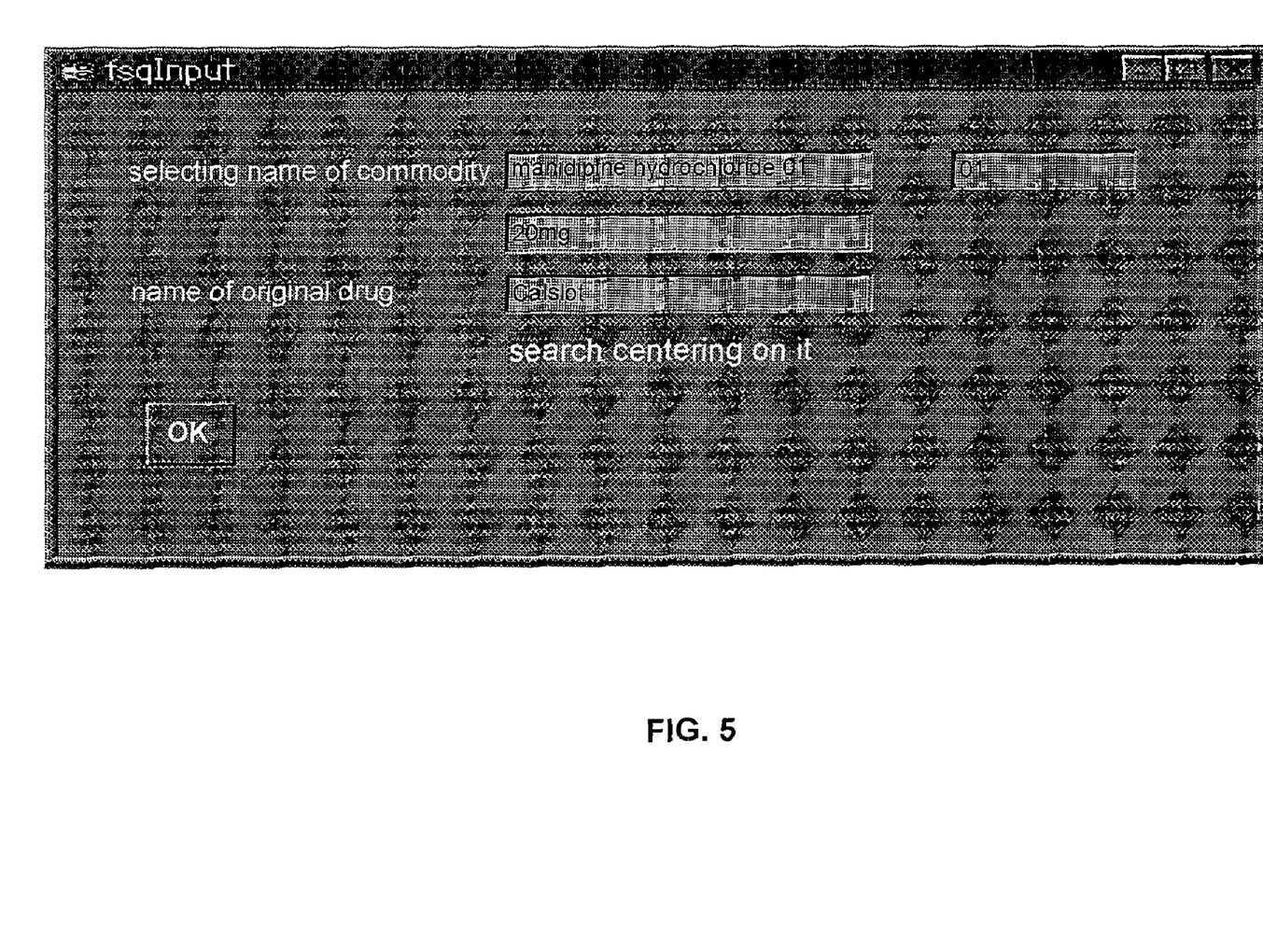
FIG. 5 is a confirmation page for an original drug.
Figure 6:
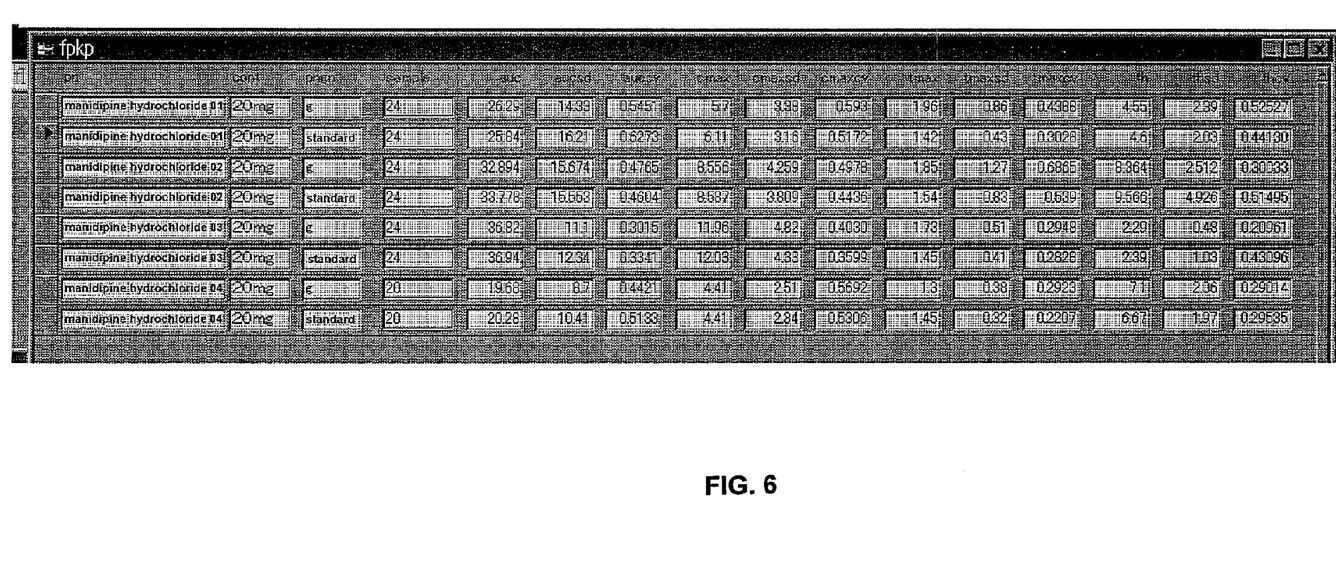
FIG. 6 is a data display page of an original drug and a corresponding generic drug.
Figure 7:
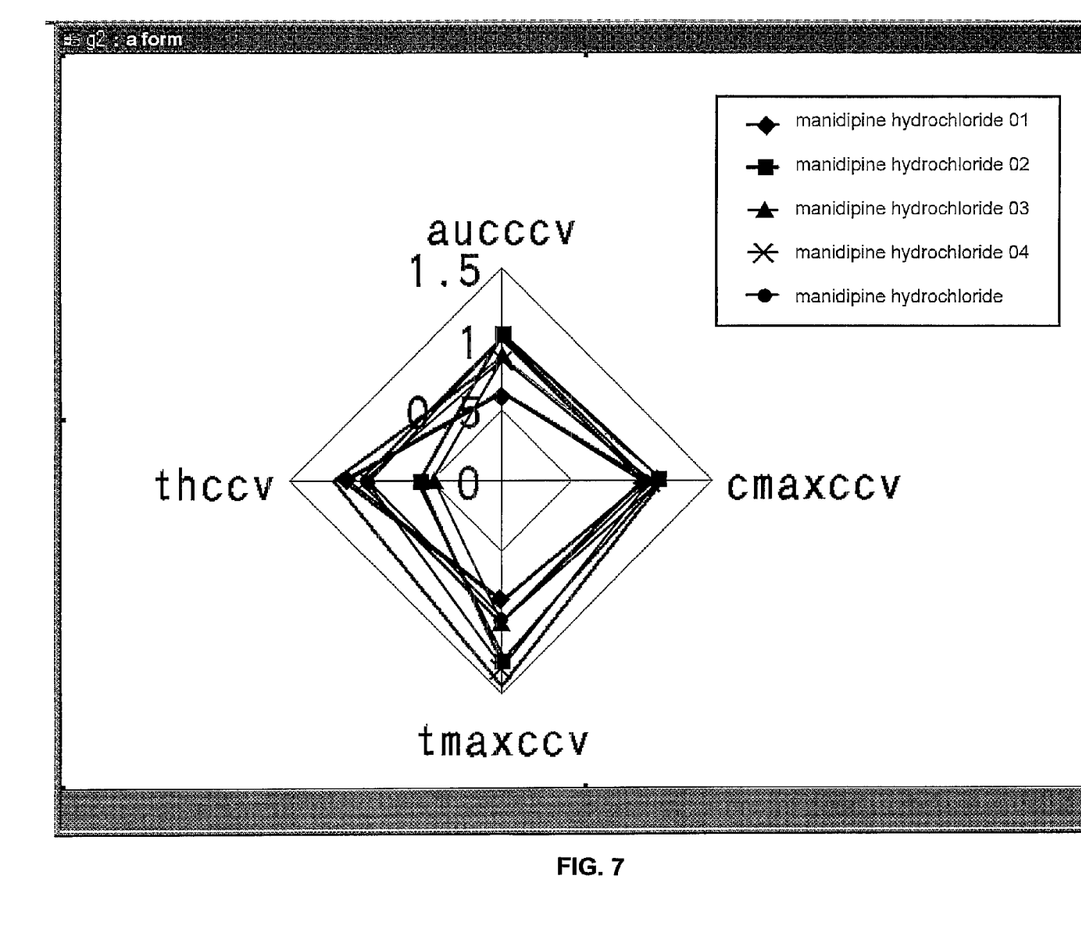
FIG. 7 is a data display page of each of the calibration coefficients of variation of an original drug and a corresponding generic drug.
Figure 8:
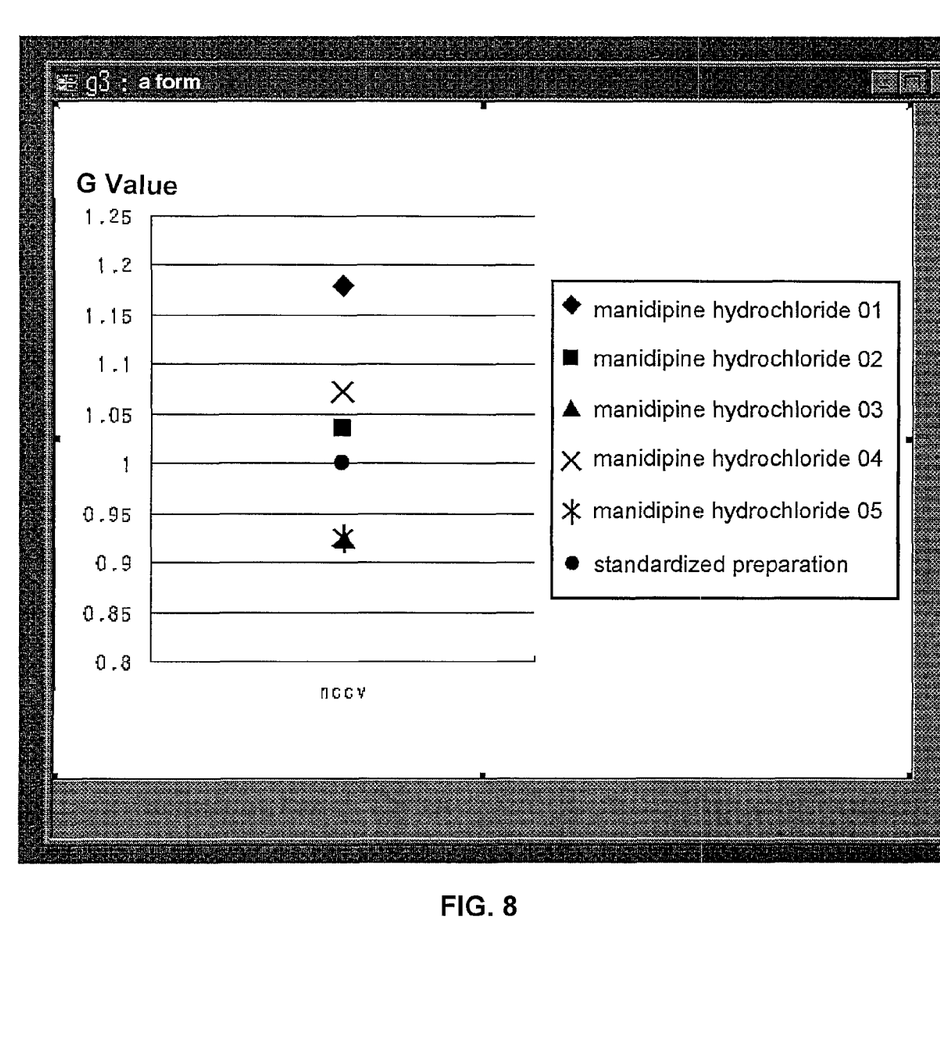
FIG. 8 is a data display page of each of G values of an original drug and a corresponding generic drug.

In FIG. 3, a flow chart for explanation of Bioequivalence Evaluation System 1 is shown. Firstly, at Step S1, by starting up the Bioequivalence Evaluation System 1, a page for searching appears on the Displaying Part 13 (FIG. 4). And by operating Inputting Part 12, an ambiguous search is made for an original drug. Then, at Step S2, as shown in FIG. 5, the original drug displayed on the Displaying Part 13 is confirmed. And then, at Step S3, by operating Inputting Part 12 and pushing on OK button, as shown in FIG. 6, with respect to the original drug and a corresponding generic drug, the maximum blood concentration (Cmax), the time-to-maximum blood concentration (Tmax), the half-life ($T_{1/2}$), the mean residence time (MRT), the blood concentration-area under the curve (AUC), each of the standard deviations (SD) and each of the variation coefficients (CV) are calculated, and such variation coefficient (CV) and each of the calibration coefficients of variation (CCV) are displayed on the Displaying Part 13. Bioequivalence between generic drugs can be compared on the basis of the degree how the value of calibration coefficient of variation (CCV) is away from one. Further, by pushing on the display exchange button (not illustrated) by means of Inputting Part 12, as shown in FIG. 7, on Displaying Part 13, each of calculation coefficients of variation (CCV) of the maximum blood concentration (Cmax), the time-to-maximum blood concentration (Tmax), the half-life ($T_{1/2}$) and the blood concentration-area under the curve (AUC) is displayed in graph, which enables bioequivalence to be easily and visually understood. And by means of Inputting Part 12, by pushing on the display exchange button (not illustrated), the graph of G values calculated according to the following expression is displayed on the Displaying Part 13 (FIG. 8). Bioequivalence can be understood with extreme ease solely by comparing the degree how these G value are away from one.

The invention is not limited to the above-mentioned embodiments of the invention. Variations thereto that is to be made without departing from the scope of the claims and that is apparent to those skilled in the art are included in the invention.

INDUSTRIAL APPLICABILITY

This invention can be used to evaluate bioequivalence of a generic drug to the corresponding original drug.

What is claimed is:

1. A non-transitory machine readable medium storing a program for enabling a computer to carry out a bioequivalence evaluation method of evaluating bioequivalence of a generic drug compared to an original drug, comprising:
   obtaining a coefficient of variation (CV) of each of the original drug and the generic drug, by dividing a standard deviation (SD) of at least one data of in vivo movement indices that numerically evaluates properties of the in vivo movement of each drug by an average value, so that CV=SD/the average value;
   obtaining a calibration coefficient of variation (CCV) of the original drug and a CCV of the generic drug, wherein each CCV is obtained by dividing said coefficient of variation (CV) by a coefficient of variation of said original drug (CVs), so that CCV=CV/CVs; and then
   evaluating bioequivalence based on the CCV values among two or more generic drugs.

2. The machine readable medium as claimed in claim 1, comprising as an in vivo movement index, said at least one data is selected from the group consisting of a maximum blood concentration (Cmax), a time-to-maximum blood concentration (Tmax), a half-life ($T_{1/2}$), a mean residence time (MRT), a blood concentration-area under the curve (AUC) in a blood concentration-time chart, and a relative absorption rate (F).

3. The machine readable medium as claimed in claim 2, wherein the CCV values are obtained by four calibration coefficients of variation that are the calibration coefficient of variation of the maximum blood concentration (Cmax), the calibration coefficient of variation of time-to-maximum blood concentration (Tmax), the calibration coefficient of variation of the half-life ($T_{1/2}$) or the calibration coefficient of variation of the mean residence time (MRT), and the calibration coefficient of variation of the blood concentration-area under the curve (AUC) or the calibration coefficient of variation of the relative absorption rate (F).

4. The machine readable medium as claimed in claim 3, wherein a G value is obtained according to the following equation (1), where CCVcmax g is the calibration coefficient of variation of Cmax of said generic drug under a fasting condition, $CCV_T$max g is the calibration coefficient of variation of Tmax of said generic drug under said fasting condition, CCVt1/2 g stands for is the calibration coefficient of variation of $T_{1/2}$ of said generic drug under said fasting condition, and $CCV_{AUC}$ g is the calibration coefficient of variation of AUC of said generic drug under said fasting condition:

$$G = \frac{\sqrt{(CCV_{Cmaxg})^2 + (CCV_{Tmaxg})^2 + (CCV_{t1/2g})^2 + (CCV_{AUCg})^2}}{2}, \quad (1)$$

and
   selecting a generic drug having the G value which is the closest to 1.

5. The machine readable medium as claimed in claim 2, wherein in a case that there are two evaluation equations that are Condition 1 and Condition 2, the G value is obtained according to the following equation (2) where CCVcmax gbm is the calibration coefficient of variation of Cmax of said generic drug under said Condition 1, $CCV_T$max gbm is the calibration coefficient of variation of Tmax of said generic drug under said Condition 1, $CCVt_{1/2}$ gbm is the calibration coefficient of variation of T1/2 of the generic drug under the Condition 1, $CCV_{AUC}$ gbm is the calibration coefficient of variation of AUC of said generic drug under said Condition 1, CCVcmax gam is the calibration coefficient of variation of Cmax of said generic drug under said Condition 2, $CCV_T$max gam is the calibration coefficient of variation of Tmax of said generic drug under said Condition 2, $CCVt_{1/2\ gam}$ is the calibration coefficient of variation of T1/2 of the generic drug under the Condition 2, $CCV_{AUC}$ gam is the calibration coefficient of variation of AUC of said generic drug under said Condition 2:

$$G = \frac{\sqrt{(CCV_{Cmaxgbm})^2 + (CCV_{Tmaxgbm})^2 + (CCV_{t1/2gbm})^2 + (CCV_{AUCgbm})^2} + \sqrt{(CCV_{Cmaxgam})^2 + (CCV_{Tmaxgam})^2 + (CCV_{t1/2gam})^2 + (CCV_{AUCgam})^2}}{(4)}, \quad (2)$$

and
   selecting a generic drug having the G value which is the closest to 1.

6. The machine readable medium as claimed in claim 1 or 2, wherein in a case that the bioequivalence is evaluated by selecting a plural number of the in vivo movement indices, the calibration coefficient of variation is obtained by multiplying each of the calibration coefficients of variation by a weighting factor for weighting.

7. A bioequivalence evaluation apparatus for evaluating bioequivalence of a generic drug to an original drug, which corresponds to the generic drug, comprising:
(a) a memory device for memorizing data of a calibration coefficient of variation (CCV) of each of the original drug and the generic drug, which is obtained by dividing a standard deviation (SD) of at least one data of in vivo movement indices that numerically evaluates properties of each drug with respect to in vivo movement thereof to obtain a coefficient of variation (CV) of each of the original drug and the generic drug by the average value and further by dividing the coefficient of variation (CV) of each of the original drug and the generic drug by a coefficient of variation of said original drug (CVs), so that CV=SD/the average value and CCV=CV/CVs;
(b) a means for selecting data of said original drug from said memory; and
(c) a means for outputting said data selected by said means for selecting data.

8. A non-transitory machine readable medium storing a program for enabling a computer to carry out a bioequivalence evaluation method of evaluating bioequivalence of a generic drug compared to a original drug, comprising:
obtaining a coefficient of variation (CV) of the original drug and a CV of the generic drug, wherein each CV is obtained by dividing a standard deviation (SD) of at least one data of in vivo movement indices that numerically evaluates properties of in vivo movement of each drug by an average value, so that CV=SD/the average value;
obtaining a calibration coefficient of variation (CCV) of the original drug and a CCV of the generic drug, wherein each CCV is obtained by dividing said coefficient of variation (CV) by a coefficient of variation of said original drug (CVs), so that CCV=CV/CVs;
obtaining a G value according to the following equation (1)

$$G = \frac{\sqrt{(CCV_{Cmaxg})^2 + (CCV_{Tmaxg})^2 + (CCV_{t1/2g})^2 + (CCV_{AUCg})^2}}{2}, \quad (1)$$

where CCVcmax g is a calibration coefficient of variation of a maximum blood concentration (Cmax) of said generic drug under a fasting condition, $CCV_T$max g is a calibration coefficient of variation of a time-to-maximum blood concentration (Tmax) of said generic drug under said fasting condition, CCVt1/2 g is a calibration coefficient of variation of the half-life ($T_{1/2}$) of said generic drug under said fasting condition, and $CCV_{AUC}$ g is the calibration coefficient of variation of a blood concentration-area under the curve (AUC) of said generic drug under said fasting condition; and
selecting a generic drug having the G value which is the closest to 1, wherein
the calibration coefficient of variation (CCV) is obtained by using a calibration coefficient of variation of Cmax in a patient's body, a calibration coefficient of variation of Tmax, a calibration coefficient of variation of $T_{1/2}$, and a calibration coefficient of variation of AUC in a blood concentration-time chart.

9. A non-transitory machine readable medium storing a program for enabling a computer to carry out a bioequivalence evaluation method of evaluating bioequivalence of a generic drug compared to a original drug, comprising:
obtaining coefficient of variation (CV) of each of the original drug and the generic drug, by dividing a standard deviation (SD) of at least one data of in vivo movement indices that numerically evaluates the properties of the in vivo movement of each drug by the average value, so that CV=SD/the average value;
obtaining the calibration coefficient of variation (CCV) of the original drug and a CCV of the generic drug, wherein each CCV is obtained by dividing said coefficient of variation (CV) by the coefficient of variation of said original drug (CVs), so that CCV=CV/CVs; and then
obtaining a G value, in a case of Condition 1 and Condition 2, according to the following equation (2), where CCVcmax gbm is a calibration coefficient of variation of a maximum blood concentration (Cmax) of said generic drug under said Condition 1, $CCV_T$max gbm is a calibration coefficient of variation of a time-to-maximum blood concentration (Tmax) of said generic drug under said Condition 1, CCVt$_{1/2}$ gbm is a calibration coefficient of variation of a half-life ($T_{1/2}$) of the generic drug under the Condition 1, $CCV_{AUC}$ gbm is a calibration coefficient of variation of a blood concentration-area under a curve (AUC) of said generic drug under said Condition 1, CCVcmax gam is a calibration coefficient of variation of Cmax of said generic drug under said Condition 2, $CCV_T$max gam is a calibration coefficient of variation of Tmax of said generic drug under said Condition 2, CCVt$_{1/2\ gam}$ is a calibration coefficient of variation of $T_{1/2}$ of the generic drug under the Condition 2, $CCV_{AUC}$ gam a calibration coefficient of variation of AUC of said generic drug under said Condition 2:

$$G = \frac{\sqrt{\begin{array}{c}(CCV_{Cmaxgbm})^2 + (CCV_{Tmaxgbm})^2 + \\ (CCV_{t1/2gbm})^2 + (CCV_{AUCgbm})^2\end{array}} + \sqrt{\begin{array}{c}(CCV_{Cmaxgam})^2 + (CCV_{Tmaxgam})^2 + \\ (CCV_{t1/2gam})^2 + (CCV_{AUCgam})^2\end{array}}}{4}, \quad (2)$$

and
selecting a generic drug having the G value which is the closest to 1, wherein
the calibration coefficient of variation (CCV) is obtained by a calibration coefficient of variation of Cmax in a patient's body, a calibration coefficient of variation of Tmax, a calibration coefficient of variation of $T_{1/2}$, and a calibration coefficient of variation of AUC in a blood concentration-time chart.

* * * * *